(12) United States Patent
Baichwal et al.

(10) Patent No.: US 7,276,250 B2
(45) Date of Patent: Oct. 2, 2007

(54) SUSTAINED RELEASE FORMULATIONS OF OXYMORPHONE

(75) Inventors: Anand R. Baichwal, Wappingers Falls, NY (US); Huai-Hung Kao, Syosset, NY (US); Troy W. McCall, Germantown, TN (US)

(73) Assignee: Penwest Pharmaceuticals Company, Danbury, CT (US)

( * ) Notice: Subject to any disclaimer, the term of this patent is extended or adjusted under 35 U.S.C. 154(b) by 216 days.

(21) Appl. No.: 10/189,932

(22) Filed: Jul. 3, 2002

(65) Prior Publication Data

US 2003/0129230 A1 Jul. 10, 2003

Related U.S. Application Data

(60) Provisional application No. 60/329,352, filed on Oct. 15, 2001, provisional application No. 60/329,426, filed on Oct. 15, 2001, provisional application No. 60/303,357, filed on Jul. 6, 2001.

(51) Int. Cl.
*A61K 9/22* (2006.01)
*A61K 9/26* (2006.01)
*A61K 9/36* (2006.01)

(52) U.S. Cl. ............ 424/468; 424/470; 424/464; 424/479; 424/480; 424/481; 424/482

(58) Field of Classification Search ............ 424/468, 424/474, 490, 475, 476, 477, 479, 480, 482, 424/491, 494, 495, 497, 498
See application file for complete search history.

(56) References Cited

U.S. PATENT DOCUMENTS

| 2,806,033 A | 9/1957 | Lewenstein et al. |
| 3,393,197 A | 7/1968 | Pachter et al. |
| 3,845,770 A | 11/1974 | Theeuwes et al. |
| 3,879,555 A | 4/1975 | Pachter et al. |
| 3,966,940 A | 6/1976 | Pachter et al. |
| 3,980,766 A | 9/1976 | Shaw et al. |
| 4,070,494 A | 1/1978 | Hoffmeister et al. |
| 4,366,159 A | 12/1982 | Magruder |
| 4,457,933 A | 7/1984 | Gordon et al. |
| 4,464,376 A | 8/1984 | Sunshine et al. |

(Continued)

FOREIGN PATENT DOCUMENTS

AU 0016639 12/1999

(Continued)

OTHER PUBLICATIONS

Staniforth, et al., "Synergistically Interacting Heterodisperse Polysaccharides—Function in Achieving Controllable Drug Delivery," *American Chemical Society*, pp. 327-350 (1993).

(Continued)

*Primary Examiner*—Lakshmi S. Channavajjala
(74) *Attorney, Agent, or Firm*—Wilmer Cutler Pickering Hale & Dorr, LLP

(57) ABSTRACT

Sustained release formulations of oxymorphone or pharmaceutically acceptable salts thereof; methods for making the sustained release formulations of oxymorphone or pharmaceutically acceptable salts thereof; and methods for using the sustained release formulations of oxymorphone or pharmaceutically acceptable salts thereof to treat patients suffering from pain are provided.

16 Claims, 1 Drawing Sheet

U.S. PATENT DOCUMENTS

| | | |
|---|---|---|
| 4,479,956 A | 10/1984 | Sunshine et al. |
| 4,486,436 A | 12/1984 | Sunshine et al. |
| 4,558,051 A | 12/1985 | Sunshine et al. |
| 4,567,183 A | 1/1986 | Sunshine et al. |
| 4,569,937 A * | 2/1986 | Baker et al. ............... 514/282 |
| 4,582,835 A | 4/1986 | Lewis et al. |
| 4,587,249 A | 5/1986 | Sunshine et al. |
| 4,599,114 A | 7/1986 | Atkinson |
| 4,656,177 A | 4/1987 | Sunshine et al. |
| 4,661,492 A | 4/1987 | Lewis et al. |
| 4,711,782 A * | 12/1987 | Okada et al. ............... 424/455 |
| 4,777,174 A | 10/1988 | Sunshine et al. |
| 4,844,909 A | 7/1989 | Goldie et al. ............... 424/480 |
| 4,861,598 A | 8/1989 | Oshlack |
| 4,935,428 A | 6/1990 | Lewis et al. |
| 4,994,276 A | 2/1991 | Baichwal et al. ........... 424/440 |
| 5,128,143 A | 7/1992 | Baichwal et al. |
| 5,135,757 A | 8/1992 | Baichwal et al. |
| 5,236,714 A | 8/1993 | Lee et al. |
| 5,399,358 A | 3/1995 | Baichwal et al. |
| 5,431,922 A | 7/1995 | Nicklasson |
| 5,455,046 A | 10/1995 | Baichwal |
| 5,470,584 A | 11/1995 | Hendrickson et al. |
| 5,478,577 A * | 12/1995 | Sackler et al. ............... 424/489 |
| 5,512,297 A | 4/1996 | Baichwal |
| 5,512,578 A | 4/1996 | Crain et al. |
| 5,543,434 A | 8/1996 | Weg |
| 5,554,387 A | 9/1996 | Baichwal |
| 5,556,837 A | 9/1996 | Nestler et al. |
| 5,567,754 A | 10/1996 | Stramel |
| 5,580,578 A | 12/1996 | Oshlack et al. ............. 424/468 |
| 5,612,053 A | 3/1997 | Baichwal et al. |
| 5,633,000 A | 5/1997 | Grossman et al. |
| 5,639,476 A | 6/1997 | Oshlack et al. ............. 424/468 |
| 5,662,933 A | 9/1997 | Baichwal et al. ........... 424/457 |
| 5,672,360 A | 9/1997 | Sackler et al. ............... 424/490 |
| 5,738,865 A | 4/1998 | Baichwal et al. |
| 5,858,388 A | 1/1999 | Grossman et al. |
| 5,891,474 A | 4/1999 | Busetti et al. ............... 424/490 |
| 5,914,131 A | 6/1999 | Merrill et al. |
| 5,948,438 A | 9/1999 | Staniforth et al. ........... 424/464 |
| 5,958,452 A | 9/1999 | Oshlack et al. ............. 424/457 |
| 5,958,458 A * | 9/1999 | Norling et al. ............. 424/490 |
| 5,958,459 A | 9/1999 | Chasin et al. ............... 424/490 |
| 5,965,161 A | 10/1999 | Oshlack et al. ............. 424/457 |
| 5,965,163 A | 10/1999 | Miller et al. ................ 424/468 |
| 5,968,551 A | 10/1999 | Oshlack et al. ............. 424/456 |
| RE36,547 E | 2/2000 | Crain et al. |
| 6,093,420 A * | 7/2000 | Baichwal ..................... 424/468 |
| 6,103,258 A | 8/2000 | Simon |
| 6,103,261 A | 8/2000 | Chasin et al. ............... 424/459 |
| 6,129,933 A | 10/2000 | Oshlack et al. ............. 424/495 |
| 6,143,322 A | 11/2000 | Sackler et al. ............... 424/459 |
| 6,143,325 A | 11/2000 | Dennis et al. |
| 6,143,353 A | 11/2000 | Oshlack et al. ............. 427/2.21 |
| 6,221,393 B1 | 4/2001 | Collaueri et al. ............ 424/469 |
| 6,228,863 B1 | 5/2001 | Palermo et al. |
| 6,245,357 B1 | 6/2001 | Edgren et al. ............... 424/473 |
| 6,248,789 B1 | 6/2001 | Weg |
| 6,261,599 B1 | 7/2001 | Oshlack et al. |
| 6,277,384 B1 | 8/2001 | Kaiko et al. |
| 6,294,195 B1 * | 9/2001 | Oshlack et al. ............. 424/457 |
| 6,296,842 B1 | 10/2001 | Jaworowicz et al. ..... 424/78.02 |
| 6,306,425 B1 | 10/2001 | Tice et al. |
| 6,309,668 B1 * | 10/2001 | Bastin et al. ............... 424/472 |
| 6,316,031 B1 | 11/2001 | Oshlack et al. ............. 424/495 |
| 6,340,475 B2 | 1/2002 | Shell et al. ................ 424/469 |
| 6,375,957 B1 | 4/2002 | Kaiko et al. |
| 6,387,394 B1 | 5/2002 | Baichwal et al. |
| 6,391,336 B1 | 5/2002 | Royer ......................... 424/468 |
| 6,413,494 B1 | 7/2002 | Lee et al. .................... 424/9.1 |
| 6,432,438 B1 | 8/2002 | Shukla ........................ 424/426 |
| 6,475,494 B2 | 11/2002 | Kaiko et al. |
| 6,495,155 B1 | 12/2002 | Tice et al. |
| 6,506,730 B1 | 1/2003 | Lee et al. |
| 6,514,531 B1 | 2/2003 | Alaux et al. |
| 6,555,127 B2 | 4/2003 | Steiner |
| 6,627,635 B2 | 9/2003 | Palermo et al. |
| 2002/0010127 A1 | 1/2002 | Oshlack et al. |
| 2002/0058673 A1 | 5/2002 | Kaiko et al. |
| 2002/0081333 A1 | 6/2002 | Oshlack et al. ............. 424/468 |
| 2002/0090345 A1 | 7/2002 | Baichwal et al. |
| 2002/0164373 A1 | 11/2002 | Maloney ..................... 424/469 |
| 2002/0165248 A1 | 11/2002 | Wimmer et al. ............ 514/282 |
| 2002/0187192 A1 | 12/2002 | Joshi et al. |
| 2003/0004177 A1 | 1/2003 | Kao et al. |
| 2003/0031712 A1 | 2/2003 | Kaiko et al. |
| 2003/0044458 A1 | 3/2003 | Wright et al. |
| 2003/0049272 A1 | 3/2003 | Joshi et al. |
| 2003/0059397 A1 | 3/2003 | Hughes |
| 2003/0064099 A1 | 4/2003 | Oshlack et al. |
| 2003/0064122 A1 | 4/2003 | Goldberg et al. |
| 2003/0065002 A1 | 4/2003 | Caruso et al. |
| 2003/0068276 A1 | 4/2003 | Hughes et al. |
| 2003/0068370 A1 | 4/2003 | Sackler |
| 2003/0068371 A1 | 4/2003 | Oshlack et al. |
| 2003/0068375 A1 | 4/2003 | Wright et al. |
| 2003/0068392 A1 | 4/2003 | Sackler |
| 2003/0069263 A1 | 4/2003 | Breder et al. |
| 2003/0073714 A1 | 4/2003 | Breder et al. |
| 2003/0091635 A1 * | 5/2003 | Baichwal et al. ........... 424/468 |
| 2003/0124061 A1 | 7/2003 | Roberts |
| 2003/0124185 A1 | 7/2003 | Oshlack et al. |
| 2003/0125347 A1 | 7/2003 | Anderson et al. |
| 2003/0129230 A1 | 7/2003 | Baichwal et al. |
| 2003/0129234 A1 | 7/2003 | Baichwal et al. ........... 424/470 |
| 2003/0143269 A1 | 7/2003 | Oshlack et al. |
| 2003/0147975 A1 | 8/2003 | Joshi et al. |
| 2003/0152638 A1 | 8/2003 | Tice et al. |
| 2003/0157167 A1 | 8/2003 | Kao et al. .................... 424/468 |
| 2003/0157168 A1 | 8/2003 | Breder et al. |
| 2003/0158264 A1 | 8/2003 | Radhakrishnan et al. |
| 2003/0163099 A1 | 8/2003 | Wermeling et al. |
| 2003/0170181 A1 | 9/2003 | Midha |
| 2003/0190362 A1 | 10/2003 | Sackler et al. |

FOREIGN PATENT DOCUMENTS

| | | |
|---|---|---|
| CA | 2314896 | 12/1998 |
| CA | 2369302 | 10/2000 |
| EP | 319243 | 11/1980 |
| EP | 360562 A2 * | 3/1990 |
| EP | 441833 | 9/1993 |
| EP | 0 636 366 | 2/1995 |
| EP | 742711 | 3/1999 |
| EP | 751766 | 10/2001 |
| EP | 1293195 | 3/2003 |
| EP | 1293209 A1 | 3/2003 |
| JP | 2003113074 | 4/2003 |
| NZ | 0505192 | 7/1999 |
| WO | WO 80/00841 | 5/1980 |
| WO | WO-80/00841 | 5/1980 |
| WO | WO-84/00488 | 2/1984 |
| WO | WO-84/00490 | 2/1984 |
| WO | WO-85/02540 | 6/1985 |
| WO | WO-85/02542 | 6/1985 |
| WO | WO-91/07950 | 6/1991 |
| WO | WO-95/20947 | 8/1995 |
| WO | WO-95/22965 | 8/1995 |
| WO | WO-96/00047 | 1/1996 |
| WO | WO-96/02251 | 2/1996 |
| WO | WO-96/04007 | 2/1996 |
| WO | WO-96/20927 | 7/1996 |
| WO | WO-97/07750 | 3/1997 |

| WO | WO-97/16172 A1 | 5/1997 |
| WO | WO-99/32119 | 7/1999 |
| WO | WO-99/32120 | 7/1999 |
| WO | WO-00/01377 | 1/2000 |
| WO | WO 00 21520 | 4/2000 |
| WO | WO-00/33835 | 6/2000 |
| WO | WO-00/38649 | 7/2000 |
| WO | WO-00/61147 | 10/2000 |
| WO | WO-01/00181 | 1/2001 |
| WO | WO 01 08661 | 2/2001 |
| WO | WO-01/12230 | 2/2001 |
| WO | WO-01/15699 | 3/2001 |
| WO | WO-01/52813 | 7/2001 |
| WO | WO-01/58447 | 8/2001 |
| WO | WO-01/58451 | 8/2001 |
| WO | WO-02/05647 | 1/2002 |
| WO | WO-02/13886 | 2/2002 |
| WO | WO-02/087558 | 11/2002 |
| WO | WO-02/092059 | 11/2002 |
| WO | WO-02/092060 | 11/2002 |
| WO | WO-02/094172 | 11/2002 |
| WO | WO-02/094254 | 11/2002 |
| WO | WO-03/007802 | 1/2003 |
| WO | WO-03/013433 | 2/2003 |
| WO | WO-03/013476 | 2/2003 |
| WO | WO-03/013479 | 2/2003 |
| WO | WO-03/013525 | 2/2003 |
| WO | WO-03/013538 | 2/2003 |
| WO | WO-03/015531 | 2/2003 |
| WO | WO-03/026743 | 4/2003 |
| WO | WO-03/039561 | 5/2003 |
| WO | WO-03/072106 | 9/2003 |

OTHER PUBLICATIONS

United States Patent and Trademark Office, Before the Board of Appeals and Interferences, "Decision on Appeal. Appeal No. 2005-0416, U.S. Appl. No. 09/970,020", Apr. 28, 2005, pp. 1-8.

Chiao, et al., Sustained-Release Drug Delivery Systems, Chapter 94.

Weiss, Derivatives of Morphine, I. 14-Hydroxydihydromorphinone, Nov. 20, 1995, vol. 77, pp. 5891-5892.

Chiao et al., "Sustained-Release Drug Delivery Systems", Remington's Pharmaceutical Sciences, Chapter 94, pp. 1660-1675, (1993).

McConville, J. T. et al., "Use of a Novel Modified TSI for the Evaluation of Controlled-Release Aerosol Formulations. I", *Drug Dev Ind Pharmacy*, vol. 26, No. 11, pp. 1191-1198, 2000.

Dhopeshwarkar et al., Evaluation of Xanthan Gum in the Preparation of Sustained Release Matrix Tablets, Drug Development and Industrial Pharmacy, 19(9), 999-1017 (1993).

\* cited by examiner

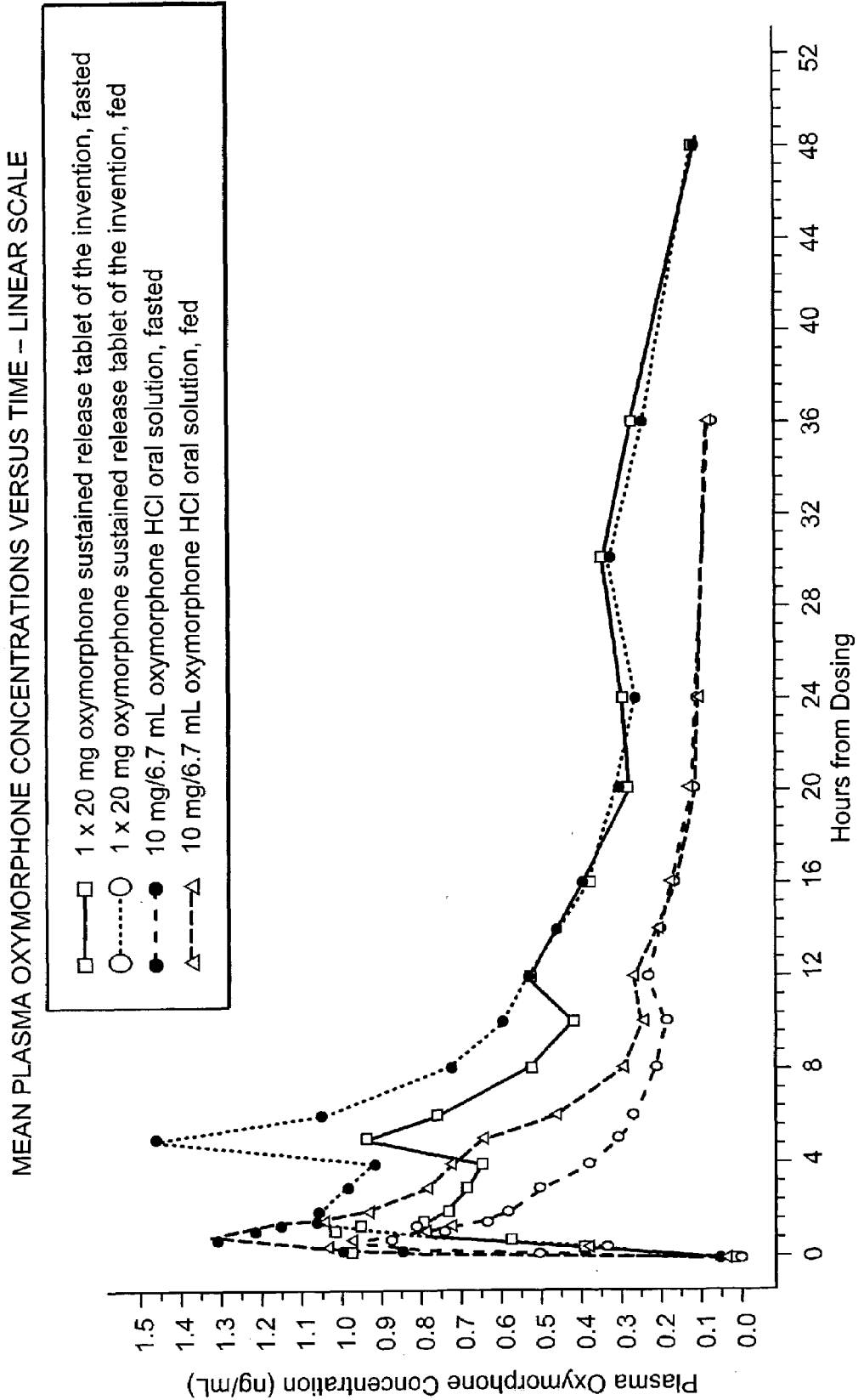

SUSTAINED RELEASE FORMULATIONS OF OXYMORPHONE

RELATED APPLICATIONS

This application claims priority to U.S. Provisional Application No. 60/329,426 filed Oct. 15, 2001, U.S. Provisional Application No. 60/329,352 filed Oct. 15, 2001, and to U.S. Provisional Application No. 60/303,357 filed Jul. 6, 2001, the disclosures of which are incorporated by reference herein in their entirety.

FIELD OF THE INVENTION

The invention provides sustained release formulations of oxymorphone and pharmaceutically acceptable salts thereof; methods for making the sustained release formulations of oxymorphone and pharmaceutically acceptable salts thereof; and methods for using the sustained release formulations of oxymorphone and pharmaceutically acceptable salts thereof to treat patients suffering from pain.

BACKGROUND OF THE INVENTION

Pain is the most frequently reported symptom and it is a common clinical problem which confronts the clinician. Many millions of people in the United States suffer from severe pain that is chronically undertreated or inappropriately managed. The clinical usefulness of the analgesic properties of opioids has been recognized for centuries, and morphine and its derivatives have been widely used for analgesia for decades in a variety of clinical pain states.

Oxymorphone HCl (14-hydroxydihydromorphinone hydrochloride) is a semi-synthetic phenanthrene-derivative opioid agonist, used in the treatment of acute and chronic pain, with analgesic efficacy comparable to other opioid analgesics. Oxymorphone is currently marketed as an injection (1 mg/ml in 1 ml ampules; 1.5 mg/ml in 1 ml ampules; 1.5 mg/ml in 10 ml multiple dose vials) for intramuscular, subcutaneous, and intravenous administration, and as 5 mg rectal suppositories. At one time, a 10 mg oral immediate release tablet formation of oxymorphone HCl was marketed. Oxymorphone HCl is metabolized principally in the liver and undergoes conjugation with glucuronic acid and reduction to 6 alpha and beta hydroxy epimers.

An important goal of analgesic therapy is to achieve continuous relief of chronic pain. Regular administration of an analgesic is generally required to ensure that the next dose is given before the effects of the previous dose have worn off. Compliance with opioids increases as the required dosing frequency decreases. Non-compliance results in suboptimal pain control and poor quality of life outcomes. Scheduled rather than "as needed" administration of opioids is currently recommended in guidelines for their use in treating chronic non-malignant pain. Unfortunately, evidence from prior clinical trials and clinical experience suggests that the short duration of action of immediate release oxymorphone would necessitate 4-hourly administrations in order to maintain optimal levels of analgesia in patients with chronic pain. Moreover, immediate release oxymorphone exhibits low oral bioavailability, because oxymorphone is extensively metabolized in the liver.

There is a need in the art for new formulations of oxymorphone that require less frequent dosing. The invention is directed to these, as well as other, important ends.

SUMMARY OF THE INVENTION

The invention provides compositions comprising oxymorphone or a pharmaceutically acceptable salt thereof and a sustained release delivery system, where the sustained release delivery system comprises at least one hydrophilic compound, at least one cross-linking agent (which may be cationic) and at least one pharmaceutical diluent. The sustained release delivery system may further comprise one or more additional hydrophobic polymers or cross-linking compounds. The compositions may optionally comprise an outer coating comprising at least one water insoluble compound, and optionally one or more plasticizers and/or water soluble compounds.

The invention provides compositions comprising an inner core and an outer sustained release coating, where the inner core comprises oxymorphone or a pharmaceutically acceptable salt thereof and the outer sustained release coating comprises at least one water insoluble compound. The outer sustained release coating may optionally further comprise one or more plasticizers and/or water soluble compounds.

The invention provides methods for treating pain in patients by administering an effective amount of any of the compositions of the invention. The pain may be moderate to severe, and may be acute or chronic.

The invention also provides methods for making such compositions.

These and other aspects of the invention are described in detail herein.

BRIEF DESCRIPTION OF THE FIGURE

FIG. 1 is a linear scale graph, without standard deviations, showing the mean oxymorphone plasma concentration versus time for patients treated with the sustained release oxymorphone tablets of the invention after fasting (A), for patients treated with sustained release oxymorphone tablets of the invention after a high fat meal (B), for patients treated with an oxymorphone solution after fasting (C), and for patients treated with an oxymorphone solution after a high fat meal (D).

DETAILED DESCRIPTION OF THE INVENTION

To overcome the difficulties associated with the very low bioavailability of the oral immediate release formulation of oxymorphone and with a 4 hourly dosing frequency of oxymorphone, the invention provides an oral sustained release formulation of oxymorphone comprising an analgesically effective amount of oxymorphone or a pharmaceutically acceptable salt thereof. The bioavailability of the oral sustained release formulations of the invention is sufficiently high that the sustained release formulations can be used to treat patients suffering from pain with only once or twice daily dosing.

The invention provides compositions comprising oxymorphone or a pharmaceutically acceptable salt thereof and a sustained release delivery system, wherein the sustained release delivery system comprises (i) at least one hydrophilic compound, at least one cross-linking agent, and at least one pharmaceutical diluent; (ii) at least one hydrophilic compound, at least one cross-linking agent, at least one pharmaceutical diluent, and at least one hydrophobic polymer; (iii) at least one hydrophilic compound, at least one cross-linking agent, at least one pharmaceutical diluent, and at least one cationic cross-linking agent different from the first cross-linking agent; (iv) at least one hydrophilic compound, at least one cross-linking agent, at least one pharmaceutical diluent, at least one cationic cross-linking compound different from the first cross-linking agent, and at least one hydrophobic polymer; (v) at least one hydrophilic compound, at least one cationic cross-linking compound, and at least one pharmaceutical diluent; or (vi) at least one hydrophilic compound, at least one cationic cross-linking compound, at least one pharmaceutical diluent, and at least one hydrophobic compound.

The oxymorphone may be homogeneously dispersed in the sustained release delivery system. Preferably, the oxymorphone or pharmaceutically acceptable salt thereof may be present in the composition in an amount of about 1 mg to about 200 mg, more preferably in an amount of about 1 mg to about 100 mg, even more preferably in an amount of about 5 mg to about 80 mg. Preferably, the sustained release delivery system may be present in the composition in an amount from about 80 mg to about 420 mg, more preferably from about 80 mg to about 360 mg, even more preferably from about 80 mg to about 200 mg. "Oxymorphone" includes oxymorphone, metabolites thereof, derivatives thereof, and/or pharmaceutically acceptable salts thereof. Metabolites of oxymorphone include, for example, 6-hydroxy-oxymorphone (e.g., 6-α-hydroxy-oxymorphone and/or 6-β-hydroxy-oxymorphone).

Oxymorphone may be in the form of any pharmaceutically acceptable salt known in the art. Exemplary pharmaceutically acceptable salts include hydrochloric, sulfuric, nitric, phosphoric, hydrobromic, maleric, malic, ascorbic, citric, tartaric, pamoic, lauric, stearic, palmitic, oleic, myristic, lauryl sulfuric, napthalinesulfonic, linoleic, linolenic acid, and the like. The hydrochloride salt of oxymorphone is preferred.

The sustained release delivery system comprises at least one hydrophilic compound. The hydrophilic compound preferably forms a gel matrix that releases the oxymorphone or the pharmaceutically acceptable salt thereof at a sustained rate upon exposure to liquids. The rate of release of the oxymorphone or the pharmaceutically acceptable salt thereof from the gel matrix depends on the drug's partition coefficient between the components of the gel matrix and the aqueous phase within the gastrointestinal tract. In the compositions of the invention, the weight ratio of oxymorphone to hydrophilic compound is generally in the range of about 1:0.5 to about 1:25, preferably in the range of about 1:0.5 to about 1:20. The sustained release delivery system generally comprises the hydrophilic compound in an amount of about 20% to about 80% by weight, preferably in an amount of about 20% to about 60% by weight, more preferably in an amount of about 40% to about 60% by weight, still more preferably in an amount of about 50% by weight.

The hydrophilic compound may be any known in the art. Exemplary hydrophilic compounds include gums, cellulose ethers, acrylic resins, polyvinyl pyrrolidone, protein-derived compounds, and mixtures thereof. Exemplary gums include heteropolysaccharide gums and homopolysaccharide gums, such as xanthan, tragacanth, pectins, acacia, karaya, alginates, agar, guar, hydroxypropyl guar, carrageenan, locust bean gums, and gellan gums. Exemplary cellulose ethers include hydroxyalkyl celluloses and carboxyalkyl celluloses. Preferred cellulose ethers include hydroxyethyl celluloses, hydroxypropyl celluloses, hydroxypropylmethyl-celluloses, carboxy methylcelluloses, and mixtures thereof. Exemplary acrylic resins include polymers and copolymers of acrylic acid, methacrylic acid, methyl acrylate and methyl methacrylate. In some embodiments, the hydrophilic compound is preferably a gum, more preferably a heteropolysaccharide gum, most preferably a xanthan gum or derivative thereof. Derivatives of xanthan gum include, for example, deacylated xanthan gum, the carboxymethyl esters of xanthan gum, and the propylene glycol esters of xanthan gum.

In another embodiment, the sustained release delivery system may further comprise at least one cross-linking agent. The cross-linking agent is preferably a compound that is capable of cross-linking the hydrophilic compound to form a gel matrix in the presence of liquids. As used herein, "liquids" includes, for example, gastrointestinal fluids and aqueous solutions, such as those used for in vitro dissolution testing. The sustained release delivery system generally comprises the cross-linking agent in an amount of about 0.5% to about 80% by weight, preferably in an amount of about 2% to about 54% by weight, more preferably in an amount of about 20% to about 30% by weight more, still more preferably in an amount of about 25% by weight.

Exemplary cross-linking agents include homopolysaccharides. Exemplary homopolysaccharides include galactomannan gums, such as guar gum, hydroxypropyl guar gum, and locust bean gum. In some embodiments, the cross-linking agent is preferably a locust bean gum or a guar gum. In other embodiments, the cross-linking agents may be alginic acid derivatives or hydrocolloids.

When the sustained release delivery system comprises at least one hydrophilic compound and at least one cross-linking agent, the ratio of hydrophilic compound to cross-linking agent may be from about 1:9 to about 9:1, preferably from about 1:3 to about 3:1.

The sustained release delivery system of the invention may comprise one or more cationic cross-linking compounds. Cationic cross-linking compound may be used instead of or in addition to the cross-linking agent. The cationic cross-linking compounds may be used in an amount sufficient to cross-link the hydrophilic compound to form a gel matrix in the presence of liquids. The cationic cross-linking compound is present in the sustained release delivery system in an amount of about 0.5% to about 30% by weight, preferably from about 5% to about 20% by weight.

Exemplary cationic cross-linking compounds include monovalent metal cations, multivalent metal cations, and inorganic salts, including alkali metal and/or alkaline earth metal sulfates, chlorides, borates, bromides, citrates, acetates, lactates, and mixtures thereof. For example, the cationic cross-linking compound may be one or more of calcium sulfate, sodium chloride, potassium sulfate, sodium carbonate, lithium chloride, tripotassium phosphate, sodium borate, potassium bromide, potassium fluoride, sodium bicarbonate, calcium chloride, magnesium chloride, sodium citrate, sodium acetate, calcium lactate, magnesium sulfate, sodium fluoride, or mixtures thereof.

When the sustained release delivery system comprises at least one hydrophilic compound and at least one cationic cross-linking compound, the ratio of hydrophilic compound to cationic cross-linking compound may be from about 1:9 to about 9:1, preferably from about 1:3 to about 3:1.

Two properties of desirable components of this system (e.g., the at least one hydrophilic compound and the at least one cross-linking agent; or the at least one hydrophilic compound and at least one cationic cross-linking compound) that form a gel matrix upon exposure to liquids are fast hydration of the compounds/agents and the ability to form a gel matrix having a high gel strength. These two properties, which are needed to achieve a slow release gel matrix, are maximized in the invention by the particular combination of compounds (e.g., the at least one hydrophilic compound and the at least one cross-linking agent; or the at least one hydrophilic compound and the at least one cationic cross-linking compound). For example, hydrophilic compounds (e.g., xanthan gum) have excellent water-wicking properties which provide fast hydration. The combination of hydrophilic compounds with materials that are capable of cross-linking the rigid helical ordered structure of the hydrophilic compound (e.g., cross-linking agents and/or cationic cross-linking compounds) thereby act synergistically to provide a higher than expected viscosity (i.e., high gel strength) of the gel matrix.

The sustained release delivery system further comprises one or more pharmaceutical diluents known in the art. Exemplary pharmaceutical diluents include monosaccharides, disaccharides, polyhydric alcohols and mixtures thereof. Preferred pharmaceutical diluents include, for example, starch, lactose, dextrose, sucrose, microcrystalline cellulose, sorbitol, xylitol, fructose, and mixtures thereof. In other embodiments, the pharmaceutical diluent is water-soluble, such as lactose, dextrose, sucrose, or mixtures thereof. The ratio of pharmaceutical diluent to hydrophilic compound is generally from about 1:8 to about 8:1, preferably from about 1:3 to about 3:1. The sustained release delivery system generally comprises one or more pharmaceutical diluents in an amount of about 20% to about 80% by weight, preferably about 35% by weight. In other embodiments, the sustained release delivery system comprises one or more pharmaceutical diluents in an amount of about 40% to about 80% by weight.

The sustained release delivery system of the invention may comprise one or more hydrophobic polymers. The hydrophobic polymers may be used in an amount sufficient to slow the hydration of the hydrophilic compound without disrupting it. For example, the hydrophobic polymer may be present in the sustained release delivery system in an amount of about 0.5% to about 20% by weight, preferably in an amount of about 2% to about 10% by weight, more preferably in an amount of about 3% to about 7% by weight, still more preferably in an amount of about 5% by weight.

Exemplary hydrophobic polymers include alkyl celluloses (e.g., $C_{1-6}$ alkyl celluloses, carboxymethylcellulose), other hydrophobic cellulosic materials or compounds (e.g., cellulose acetate phthalate, hydroxypropylmethylcellulose phthalate), polyvinyl acetate polymers (e.g., polyvinyl acetate phthalate), polymers or copolymers derived from acrylic and/or methacrylic acid esters, zein, waxes, shellac, hydrogenated vegetable oils, and mixtures thereof. The hydrophobic polymer is preferably methyl cellulose, ethyl cellulose or propyl cellulose, more preferably ethyl cellulose.

The compositions of the invention may be further admixed with one or more wetting agents (such as polyethoxylated castor oil, polyethoxylated hydrogenated castor oil, polyethoxylated fatty acid from castor oil, polyethoxylated fatty acid from hydrogenated castor oil) one or more lubricants (such as magnesium stearate, sodium stearyl fumarate, and the like), one or more buffering agents, one or more colorants, and/or other conventional ingredients.

In other embodiments, the invention provides oral sustained release solid dosage formulations comprising from about 1 mg to 200 mg oxymorphone hydrochloride, preferably from about 5 mg to about 80 mg oxymorphone hydrochloride; and about 80 mg to about 200 mg of a sustained release delivery system, preferably from about 120 mg to about 200 mg of a sustained release delivery system, more preferably about 160 mg of a sustained release delivery system; where the sustained release delivery system comprises about 8.3 to about 41.7% locust bean gum, preferably about 25% locust bean gum; about 8.3 to about 41.7% xanthan gum, preferably about 25% xanthan gum; about 20 to about 55% dextrose, preferably about 35% dextrose; about 5 to about 20% calcium sulfate dihydrate, preferably about 10% calcium sulfate dihydrate; and about 2 to 10% ethyl cellulose, preferably about 5% ethyl cellulose.

In other embodiments, the invention provides oral sustained release solid dosage formulations comprising from about 1 mg to 200 mg oxymorphone hydrochloride, preferably from about 5 mg to about 80 mg oxymorphone hydrochloride; and about 200 mg to about 420 mg of a sustained release delivery system, preferably from about 300 mg to about 420 mg of a sustained release delivery system, more preferably about 360 mg of a sustained release delivery system; where the sustained release delivery system comprises about 8.3 to about 41.7% locust bean gum, preferably about 25% locust bean gum; about 8.3 to about 41.7% xanthan gum, preferably about 25% xanthan gum; about 20 to about 55% dextrose, preferably about 35% dextrose; about 5 to about 20% calcium sulfate dihydrate, preferably about 10% calcium sulfate dihydrate; and about 2 to 10% ethyl cellulose, preferably about 5% ethyl cellulose.

The sustained release formulations of oxymorphone are preferably orally administrable solid dosage formulations which may be, for example, tablets, capsules comprising a plurality of granules, sublingual tablets, powders, or granules; preferably tablets. The tablets may be an enteric coating or a hydrophilic coating.

The sustained release delivery system in the compositions of the invention may be prepared by dry granulation or wet granulation, before the oxymorphone or pharmaceutically acceptable salt thereof is added, although the components may be held together by an agglomeration technique to produce an acceptable product. In the wet granulation technique, the components (e.g., hydrophilic compounds, cross-linking agents, pharmaceutical diluents, cationic cross-linking compounds, hydrophobic polymers, etc.) are mixed together and then moistened with one or more liquids (e.g., water, propylene glycol, glycerol, alcohol) to produce a moistened mass which is subsequently dried. The dried mass is then milled with conventional equipment into granules of the sustained release delivery system. Thereafter, the sustained release delivery system is mixed in the desired amounts with the oxymorphone or the pharmaceutically acceptable salt thereof and, optionally, one or more wetting agents, one or more lubricants, one or more buffering agents, one or more coloring agents, or other conventional ingredients, to produce a granulated composition. The sustained release delivery system and the oxymorphone may be blended with, for example, a high shear mixer. The oxymorphone is preferably finely and homogeneously dispersed in the sustained release delivery system. The granulated composition, in an amount sufficient to make a uniform batch of tablets, is subjected to tableting in a conventional production scale tableting machine at normal compression pressures, i.e., about 2,000-16,000 psi. The mixture should not be compressed to a point where there is subsequent difficulty with hydration upon exposure to liquids.

The average particle size of the granulated composition is from about 50 μm to about 400 μm, preferably from about 185 μm to about 265 μm. The average density of the granulated composition is from about 0.3 g/ml to about 0.8 g/ml, preferably from about 0.5 g/ml to about 0.7 g/ml. The tablets formed from the granulations are generally from about 6 to about 8 kg hardness. The average flow of the granulations are from about 25 to about 40 g/sec.

In other embodiments, the invention provides sustained release coatings over an inner core comprising oxymorphone or a pharmaceutically acceptable salt thereof. For example, the inner core comprising oxymorphone or a pharmaceutically acceptable salt thereof may be coated with a sustained release film which, upon exposure to liquids, releases the oxymorphone or the pharmaceutically acceptable salt thereof from the core at a sustained rate.

In one embodiment, the sustained release coating comprises at least one water insoluble compound. The water insoluble compound is preferably a hydrophobic polymer. The hydrophobic polymer may be the same as or different from the hydrophobic polymer used in the sustained release delivery system. Exemplary hydrophobic polymers include alkyl celluloses (e.g., $C_{1-6}$ alkyl celluloses, carboxymethylcellulose), other hydrophobic cellulosic materials or compounds (e.g., cellulose acetate phthalate, hydroxypropylmethylcellulose phthalate), polyvinyl acetate polymers (e.g., polyvinyl acetate phthalate), polymers or copolymers derived from acrylic and/or methacrylic acid esters, zein, waxes (alone or in admixture with fatty alcohols), shellac, hydrogenated vegetable oils, and mixtures thereof. The hydrophobic polymer is preferably, methyl cellulose, ethyl cellulose or propyl cellulose, more preferably ethyl cellulose. The sustained release formulations of the invention may be coated with a water insoluble compound to a weight gain from about 1 to about 20% by weight.

The sustained release coating may further comprise at least one plasticizer such as triethyl citrate, dibutyl phthalate, propylene glycol, polyethylene glycol, or mixtures thereof.

The sustained release coating may also contain at least one water soluble compound, such as polyvinylpyrrolidones, hydroxypropylmethylcelluloses, or mixtures thereof. The sustained release coating may comprise at least one water soluble compound in an amount from about 1% to about 6% by weight, preferably in an amount of about 3% by weight.

The sustained release coating may be applied to the oxymorphone core by spraying an aqueous dispersion of the water insoluble compound onto the oxymorphone core. The oxymorphone core may be a granulated composition made, for example, by dry or wet granulation of mixed powders of oxymorphone and at least one binding agent; by coating an inert bead with oxymorphone and at least one binding agent; or by spheronizing mixed powders of oxymorphone and at least one spheronizing agent. Exemplary binding agents include hydroxypropylmethylcelluloses. Exemplary spheronizing agents include microcrystalline celluloses. The inner core may be a tablet made by compressing the granules or by compressing a powder comprising oxymorphone or the pharmaceutically acceptable salt thereof.

In other embodiments, the compositions comprising oxymorphone or a pharmaceutically acceptable salt thereof and a sustained release delivery system, as described herein, are coated with a sustained release coating, as described herein. In still other embodiments, the compositions comprising oxymorphone or a pharmaceutically acceptable salt thereof and a sustained release delivery system, as described herein, are coated with a hydrophobic polymer, as described herein. In still other embodiments, the compositions comprising oxymorphone or a pharmaceutically acceptable salt thereof and a sustained release delivery system, as described herein, are coated with an enteric coating, such as cellulose acetate phthalate, hydroxypropylmethylcellulose phthalate, polyvinylacetate phthalate, methacrylic acid copolymer, shellac, hydroxypropylmethylcellulose succinate, cellulose acetate trimelliate, or mixtures thereof. In still other embodiments, the compositions comprising oxymorphone or a pharmaceutically acceptable salt thereof and a sustained release delivery system, as described herein, are coated with a hydrophobic polymer, as described herein, and further coated with an enteric coating, as described herein. In any of the embodiments described herein, the compositions comprising oxymorphone or a pharmaceutically acceptable salt thereof and a sustained release delivery system, as described herein, may optionally be coated with a hydrophilic coating which may be applied above or beneath the sustained release film, above or beneath the hydrophobic coating, and/or above or beneath the enteric coating. Preferred hydrophilic coatings comprise hydroxypropylmethylcellulose.

The invention provides methods for treating pain by administering an effective amount of the sustained release formulations of oxymorphone to a patient in need thereof. An effective amount is an amount sufficient to eliminate all pain or to alleviate the pain (i.e., reduce the pain compared to the pain present prior to administration of the oxymorphone sustained release formulation). "Sustained release" means that the oxymorphone or pharmaceutically acceptable salt thereof is released from the formulation at a controlled rate so that therapeutically beneficial blood levels (but below toxic levels) of the oxymorphone or pharmaceutically acceptable salt thereof are maintained over an extended period of time. The sustained release formulations of oxymorphone are administered in an amount sufficient to alleviate pain for an extended period of time, preferably about 8 hours to about 24 hours, more preferably for a period of about 12 hours to about 24 hours. The oxymorphone sustained release oral solid dosage formulations of the invention may be administered one to four times a day, preferably once or twice daily, more preferably once daily. The pain may be minor to moderate to severe, and is preferably moderate to severe. The pain may be acute or chronic. The pain may be associated with, for example, cancer, autoimmune diseases, infections, surgical traumas, accidental traumas or osteoarthritis. The patient may be an animal, preferably a mammal, more preferably a human.

In certain embodiments, upon oral ingestion of the oxymorphone sustained release formulation and contact of the formulation with gastrointestinal fluids, the sustained release formulation swells and gels to form a hydrophilic gel matrix from which the oxymorphone is released. The swelling of the gel matrix causes a reduction in the bulk density of the formulation and provides the buoyancy necessary to allow the gel matrix to float on the stomach contents to provide a slow delivery of the oxymorphone. The hydrophilic matrix, the size of which is dependent upon the size of the original formulation, can swell considerably and become obstructed near the opening of the pylorus. Since the oxymorphone is dispersed throughout the formulation (and consequently throughout the gel matrix), a constant amount of oxymorphone can be released per unit time in vivo by dispersion or erosion of the outer portions of the hydrophilic gel matrix. The process continues, with the gel matrix remaining buoyant in the stomach, until substantially all of the oxymorphone is released.

In certain embodiments, the chemistry of certain of the components of the formulation, such as the hydrophilic compound (e.g., xanthan gum), is such that the components are considered to be self-buffering agents which are substantially insensitive to the solubility of the oxymorphone and the pH changes along the length of the gastrointestinal tract. Moreover, the chemistry of the components is believed to be similar to certain known muco-adhesive substances, such as polycarbophil. Muco-adhesive properties are desirable for buccal delivery systems. Thus, the sustained release formulation can loosely interact with the mucin in the gastrointestinal tract and thereby provide another mode by which a constant rate of delivery of the oxymorphone is achieved.

The two phenomenon discussed above (buoyancy and muco-adhesive properties) are mechanisms by which the sustained release formulations of the invention can interact with the mucin and fluids of the gastrointestinal tract and provide a constant rate of delivery of the oxymorphone.

When measured by USP Procedure Drug Release USP 23 (incorporated by reference herein in its entirety), the sustained release formulations of the invention exhibit an in vitro dissolution rate of about 15% to about 50% by weight oxymorphone after 1 hour, about 45% to about 80% by weight oxymorphone after 4 hours, and at least about 80% by weight oxymorphone after 10 hours. The in vitro and in vivo release characteristics of the sustained release formulations of the invention may be modified using mixtures of one or more different water insoluble and/or water soluble compounds, using different plasticizers, varying the thickness of the sustained release film, including providing release-modifying compounds in the coating, and/or by providing passageways through the coating.

When administered orally to patients the sustained release formulations of the invention exhibit the following in vivo characteristics: (a) a peak plasma level of oxymorphone occurs within about 2 to about 6 hours after administration; (b) the duration of the oxymorphone analgesic effect is about 8 to about 24 hours; and (c) the relative oxymorphone bioavailability is about 0.5 to about 1.5 compared to an orally administered aqueous solution of oxymorphone.

While the compositions of the invention may be administered as the sole active pharmaceutical compound in the methods described herein, they can also be used in combination with one or more compounds which are known to be therapeutically effective against pain.

The invention also provides pharmaceutical kits comprising one or more containers filled with one or more of the compositions of the invention. The kits may further comprise other pharmaceutical compounds known in the art to be therapeutically effective against pain, and instructions for use.

EXAMPLES

The following examples are for purposes of illustration only and are not intended to limit the scope of the appended claims.

Examples 1 and 2

Two sustained release delivery systems were prepared by dry blending xanthan gum, locust bean gum, calcium sulfate dehydrate, and dextrose in a high speed mixed/granulator for 3 minutes. A slurry was prepared by mixing ethyl cellulose with alcohol. While running choppers/impellers, the slurry was added to the dry blended mixture, and granulated for another 3 minutes. The granulation was then dried to a LOD (loss on drying) of less than about 10% by weight. The granulation was then milled using 20 mesh screen. The relative quantities of the ingredients are listed in Table 1.

TABLE 1

| Sustained Release Delivery System Excipient | Example 1 % | Example 2 % |
|---|---|---|
| Locust Bean Gum, FCC | 25.0 | 30.0 |
| Xanthan Gum, NF | 25.0 | 30.0 |
| Dextrose, USP | 35.0 | 40.0 |
| Calcium Sulfate Dihydrate, NF | 10.0 | 0.0 |
| Ethylcellulose, NF | 5.0 | 0.0 |
| Alcohol, SD3A (Anhydrous)[1] | (10)[1] | (20.0)[1] |
| Total | 100.0 | 100.0 |

[1]Volatile, removed during processing

Examples 3 to 7

A series of tablets containing different amounts of oxymorphone hydrochloride were prepared using the sustained release delivery system of Example 1. The quantities of ingredients per tablet are listed in Table 2.

TABLE 2

| Component | Ex. 3 mg | Ex. 4 mg | Ex. 5 mg | Ex. 6 mg | Ex. 7 mg |
|---|---|---|---|---|---|
| Oxymorphone HCl, USP | 5 | 10 | 20 | 40 | 80 |
| Sustained release delivery system | 160 | 160 | 160 | 160 | 160 |
| Silicified microcrystalline cellulose, N.F. | 20 | 20 | 20 | 20 | 20 |
| Sodium stearyl fumarate, NF | 2 | 2 | 2 | 2 | 2 |
| Total weight | 187 | 192 | 202 | 222 | 262 |
| OPADRY ® (colored) | 7.48 | 7.68 | 8.08 | 8.88 | 10.48 |
| OPADRY ® (clear) | 0.94 | 0.96 | 1.01 | 1.11 | 1.31 |

Examples 8 and 9

Two batches of tablets were prepared as described above for Examples 1-7, using the sustained release delivery system of Example 1. One batch was formulated to provide relatively fast sustained release, the other batch was formulated to provide relatively slow sustained release. Compositions of the tablets are shown in Table 3.

TABLE 3

| Ingredients | Example 8 slow release mg/tablet | Example 9 fast release mg/tablet |
|---|---|---|
| Oxymorphone HCl, USP | 20 | 20 |
| Sustained Release Delivery System | 360 | 160 |
| Silicified Microcrystalline Cellulose, NF | 20 | 20 |
| Sodium stearyl fumarate, NF | 4 | 2 |
| Coating (color) | 12.12 | 12.12 |
| Total weight | 416.12 | 214.12 |

The tables of Examples 8 and 9 were tested for in vitro release rate according to USP Procedure Drug Release USP 23. The results are shown in Table 4.

TABLE 4

| Time (hr) | Example 8 slow release | Example 9 fast release |
|---|---|---|
| 0.5 | 18.8% | 21.3% |
| 1 | 27.8% | 32.3% |

TABLE 4-continued

| Time (hr) | Example 8 slow release | Example 9 fast release |
|---|---|---|
| 2 | 40.5% | 47.4% |
| 3 | 50.2% | 58.5% |
| 4 | 58.1% | 66.9% |
| 5 | 64.7% | 73.5% |
| 6 | 70.2% | 78.6% |
| 8 | 79.0% | 86.0% |
| 10 | 85.3% | 90.6% |
| 12 | 89.8% | 93.4% |

Example 10

Clinical Study

A clinical study was conducted to (1) assess the relative bioavailability (rate and extent of absorption) of oxymorphone sustained release (20 mg) (fast release formulation of Example 9) compared to oral solution oxymorphone (10 mg) under fasted conditions, (2) to assess the relative bioavailability of oxymorphone sustained release (20 mg) compared to oral solution oxymorphone (10 mg) under fed conditions, (3) to assess the relative bioavailability of oxymorphone sustained release (20 mg) fed compared to oxymorphone sustained release (20 mg) fasted, (4) to assess the relative bioavailability of oral solution oxymorphone fed compared to oral solution oxymorphone fasted, and (5) to assess the relative safety and tolerability of sustained release oxymorphone (20 mg) under fed and fasted conditions.

This study had a single-center, open-label, analytically blinded, randomized, four-way crossover design. Subjects randomized to Treatment A and Treatment C, as described below, were in a fasted state following a 10-hour overnight fast. Subjects randomized to Treatment B and Treatment D, as described below, were in the fed state, having had a high fat meal, completed ten minutes prior to dosing. There was a 14-day washout interval between the four dose administrations. The subjects were confined to the clinic during each study period. Subjects assigned to receive Treatment A and Treatment B were discharged from the clinic on Day 3 following the 48-hour procedures, and subjects assigned to receive Treatment C and Treatment D were discharged from the clinic on Day 2 following the 36-hour procedures. On Day 1 of each study period the subjects received one of four treatments:

Treatments A and B were of oxymorphone sustained release 20 mg tablets. Subjects randomized to Treatment A received a single oral dose of one 20 mg oxymorphone sustained release tablet taken with 240 ml of water after a 10-hour fasting period. Subjects randomized to Treatment B received a single oral dose of one 20 mg oxymorphone sustained release tablet taken with 240 ml of water 10 minutes after a standardized high fat meal.

Treatments C and D were of oxymorphone HCl solutions, USP, 1.5 mg/ml injection 10 ml vials. Subjects randomized to Treatment C received a single oral dose of 10 mg (6.7 ml) oxymorphone solution taken with 240 ml of water after a 10-hour fasting period. Subjects randomized to Treatment D received a single oral dose of 10 mg (6.7 mil) oxymorphone solution taken with 240 ml of water 10 minutes after a standardized high-fat meal.

A total of 28 male subjects were enrolled in the study, and 24 subjects completed the study. The mean age of the subjects was 27 years (range of 19 through 38 years), the mean height of the subjects was 69.6 inches (range of 64.0 through 75.0 inches), and the mean weight of the subjects was 169.0 pounds (range 117.0 through 202.0 pounds). The subjects were not to consume any alcohol-, caffeine-, or xanthine-containing foods or beverages for 24 hours prior to receiving study medication for each study period. Subjects were to be nicotine and tobacco free for at least 6 months prior to enrolling in the study. In addition, over-the-counter medications were prohibited 7 days prior to dosing and during the study. Prescription medications were not allowed 14 days prior to dosing and during the study.

The subjects were screened within 14 days prior to study enrollment. The screening procedure included medical history, physical examination (height, weight, frame size, vital signs, and ECG), and clinical laboratory tests (hematology, serum chemistry, urinalysis, HIV antibody screen, Hepatitis B surface antigen screen, Hepatitis C antibody screen, and a screen for cannabinoids).

During the study, the subjects were to remain in an upright position (sitting or standing) for 4 hours after the study drug was administered. Water was restricted 2 hours predose to 2 hours postdose. During the study, the subjects were not allowed to engage in any strenuous activity.

Subjects reported to the clinic on the evening prior to each dosing. The subjects then observed a 10-hour overnight fast. On Day 1, subjects randomized to Treatment B and Treatment D received a high-fat breakfast within 30 minutes prior to dosing. A standardized meal schedule was then initiated with lunch 4 hours postdose, dinner 10 hours postdose, and a snack 13 hours postdose. On Day 2, a standardized meal was initiated with breakfast at 0815, lunch at 1200, and dinner at 1800. Subjects randomized to Treatment A and Treatment B received a snack at 2100 on Day 2.

Vital signs (sitting for 5 minutes and consisting of blood pressure, pulse, respiration, and temperature), and 12-lead ECG were assessed at the—13 hour point of each check-in period and at the completion of each period. A clinical laboratory evaluation (hematology, serum chemistry, urinalysis) and a brief physical examination were performed at the—13 hour of each check-in period and at the completion of the each period. Subjects were instructed to inform the study physician and/or nurses of any adverse events that occurred during the study.

Blood samples (7 ml) were collected during each study period at the 0 hour (predose), and at 0.5, 1, 1.5, 2, 3, 4, 5, 6, 8, 10, 12, 14, 16, 20, 24, 30, 36, and 48 hours post-dose (19 samples) for subjects randomized to Treatment A and Treatment B. Blood samples (7 ml) were collected during each study period at the 0 hour (predose), and at 0.25, 0.5, 0.75, 1, 1.25, 1.5, 1.75, 2, 3, 4, 5, 6, 8, 10, 12, 14, 16, 20, and 36 hours post-dose (21 samples) for subjects randomized to Treatment C and Treatment D. A total of 80 blood samples (560 ml) per subject were drawn during the study for drug analysis. Plasma samples were separated by centrifugation, and then frozen at −70° C., and kept frozen until assayed.

An LC/MS/MS method was developed and validated for the determination of oxymorphone in human EDTA plasma. Samples were spiked with internal standard, $d_3$-oxymorphone, and placed on the RapidTrace® (Zymark Corporation, Hopkinton, Mass.) for automatic solid phase extraction. Extracts were dried under nitrogen and reconstituted with acetonitrile before injection onto an LC/MS/MS. The Perkin Elmer Sciex API III+, or equivalent, using a turbo ion spray interface was employed in this study. Positive ions were monitored in the MRM mode.

The pharmacokinetic parameters shown in Table 5 were computed from the plasma oxymorphone concentration-time data.

TABLE 5

| | |
|---|---|
| AUC(0-t) | Area under the drug concentration-time curve from time zero to the time of the last quantifiable concentration (Ct), calculated using linear trapezoidal summation. |
| AUC(0-inf) | Area under the drug concentration-time curve from time zero to infinity. AUC(0-inf) = AUC(0-t) + Ct/Kel, where Kel is the terminal elimination rate constant. |
| AUC(0-24) | Partial area under the drug concentration-time curve from time zero to 24 hours. |
| Cmax | Maximum observed drug concentration. |
| Tmax | Time of the observed maximum drug concentration. |
| Kel | Elimination rate constant based on the linear regression of the terminal linear portion of the LN(concentration) time curve. |
| T1/2el | Half life, the time required for the concentration to decline by 50%, calculated as LN(2)/Kel |

Terminal elimination rate constants were computed using linear regression of a minimum of three time points, at least two of which were consecutive. Kel values for which correlation coefficients were less than or equal to 0.8 were not reported in the pharmacokinetic parameter tables or included in the statistical analysis. Thus, T1/2el, AUC(0-inf), Cl/F, MRT, and LN-transformed T1/2el, AUC(0-inf), and Cl/F were also not reported in these cases.

A parametric (normal-theory) general linear model was applied to each of the above parameters (excluding Tmax and Frel), and the LN-transformed parameters $C_{max}$, AUC (0-24), AUC(0-t), AUC(0-inf), Cl/F, and T1/2el. Initially, the analysis of variance (ANOVA) model included the following factors: treatment, sequence, subject within sequence, period, and carryover effect. If carryover effect was not significant, it was dropped from the model. The sequence effect was tested using the subject within sequence mean square, and all other main effects were tested using the residual error (error mean square). The following treatment comparisons of relative rate and extent of absorption were made: Treatment B versus Treatment A, Treatment A versus Treatment C (dose normalized to 20 mg), Treatment B versus Treatment D (dose normalized to 20 mg), and Treatment D versus Treatment C (dose normalized to 20 mg for both treatments). The 90% confidence intervals of the ratios of the treatment least squares parameter means were calculated. Tmax was analyzed using the Wilcoxon Signed Ranks test. Summary statistics were presented for Frel.

Plasma oxymorphone concentrations were listed by subject at each collection time and summarized using descriptive statistics. Pharmacokinetic parameters were also listed by subject and summarized using descriptive statistics.

A total of 26 analytical runs were required to process the clinical samples from this study. Of these 26 analytical runs, 26 were acceptable for oxymorphone. Standard curves for the 26 analytical runs in EDTA plasma used in this study covered a range of 0.0500 to 20.000 mg/ml with a limit of quantitation of 0.0500 ng/ml for both compounds. Quality control samples analyzed with each analytical run had coefficients of variation less than or equal to 14.23% for oxymorphone.

A total of 28 subjects received at least one treatment. Only subjects who completed all 4 treatments were included in the summary statistics and statistical analysis.

The mean oxymorphone plasma concentration versus time curves for Treatments A, B, C, and D are presented in FIG. 1 (linear scale, without standard deviation).

Individual concentration versus time curves were characterized by multiple peaks which occurred in the initial 12-hour period following the dose. In addition, a small "bump" in plasma oxymorphone concentration was generally observed in the 24 to 48 hour post-dose period.

The arithmetic means of the plasma oxymorphone pharmacokinetic parameters and the statistical comparisons for Treatment B versus Treatment A are summarized in Table 6.

TABLE 6

Summary of the Pharmacokinetic Parameters of Plasma Oxymorphone for Treatments B and A

| | Plasma Oxymorphone | | | | | |
|---|---|---|---|---|---|---|
| | Treatment A | | Treatment B | | | |
| Pharmacokinetic Parameters | Arithmetic Mean | SD | Arithmetic Mean | SD | 90% CI | Mean Ratio |
| Cmax(ng/ml) | 1.7895 | 0.6531 | 1.1410 | 0.4537 | 125.4-191.0 | 158.2 |
| Tmax(hr) | 5.65 | 9.39 | 5.57 | 7.14 | | |
| Auc(0-24)(ng * hr/ml) | 14.27 | 4.976 | 11.64 | 3.869 | 110.7-134.0 | 122.3 |
| AUC(O-t)(ng * hr/ml) | 19.89 | 6.408 | 17.71 | 8.471 | 100.2-123.6 | 111.9 |
| AUC(O-inf) (ng * hr/ml) | 21.29 | 6.559 | 19.29 | 5.028 | 105.3-133.9 | 119.6 |
| T 1/2el(hr) | 12.0 | 3.64 | 12.3 | 3.99 | 57.4-155.2 | 106.3 |

Treatment B = 1 × 20 mg oxymorphone sustained release Tablet, Fed: test
Treatment A = 1 × 20 mg oxymorphone sustained release Tablet, Fasted: reference The arithmetic means of the plasma oxymorphone pharmacokinetic parameters and the statistical comparisons for Treatment A versus Treatment C are summarized in Table 7.

TABLE 7

Summary of the Pharmacokinetic Parameters of Plasma Oxymorphone for Treatments A and C

| Pharmacokinetic Parameters | Plasma Oxymorphone | | | | | |
|---|---|---|---|---|---|---|
| | Treatment A | | Treatment C | | | |
| | Arithmetic Mean | SD | Arithmetic Mean | SD | 90% CI | Mean Ratio |
| Cmax(ng/ml) | 1.1410 | 0.4537 | 2.2635 | 1.0008 | 33.4-66.0 | 49.7 |
| Tmax(hr) | 5.57 | 7.14 | 0.978 | 1.14 | | |
| Auc(0-24)(ng * hr/ml) | 11.64 | 3.869 | 12.39 | 4.116 | 82.8-104.6 | 93.7 |
| AUC(0-I)(ng * hr/ml | 17.71 | 8.471 | 14.53 | 4.909 | 107.7-136.3 | 122.0 |
| AUC(0-inf) (ng * hr/ml) | 19.29 | 5.028 | 18.70 | 6.618 | 80.2-108.4 | 94.3 |
| T 1/2el(hr) | 12.3 | 3.99 | 16.2 | 11.4 | 32.9-102.1 | 67.5 |

Treatment A = 1 × 20 mg oxymorphone sustained release Tablet, Fasted: test
Treatment C = 10 mg/6.7 ml oxymorphone HCl Oral Solution, Fasted: Dose Normalized to 20 ng: reference.

The arithmetic means of the plasma oxymorphone pharmacokinetic parameters and the statistical comparisons for Treatment D versus Treatment C are summarized in Table 8.

TABLE 8

Summary of the Pharmacokinetic Parameters of Plasma Oxymorphone for Treatments A and C

| Pharmacokinetic Parameters | Plasma Oxymorphone | | | | | |
|---|---|---|---|---|---|---|
| | Treatment B | | Treatment D | | | |
| | Arithmetic Mean | SD | Arithmetic Mean | SD | 90% CI | Mean Ratio |
| Cmax(ng/ml) | 1.7895 | 0.6531 | 3.2733 | 1.3169 | 42.7-65.0 | 50.0 |
| Tmax(hr) | 5.65 | 9.39 | 1.11 | 0.768 | | |
| Auc(0-24)(ng * hr/ml) | 14.27 | 4.976 | 17.30 | 5.259 | 74.4-90.1 | 82.2 |
| AUC(0-t)(ng * hr/ml) | 19.89 | 6.408 | 19.28 | 6.030 | 92.5-114.1 | 103.3 |
| AUC(0-inf) (ng * hr/ml) | 21.29 | 6.559 | 25.86 | 10.03 | 75.0-95.2 | 85.1 |
| T 1/2el(hr) | 12.0 | 3.64 | 20.6 | 19.3 | 31.9-86.1 | 59.0 |

Treatment B = 1 × 20 mg oxymorphone sustained release Tablet, Fed: test
Treatment D = 10 mg/6.7 ml oxymorphone HCl Oral Solution, Fed: Dose Normalized to 20 mg: reference.

The arithmetic means of the plasma oxymorphone pharmacokinetic parameters and the statistical comparisons for Treatment D versus Treatment C are summarized in Table 9.

TABLE 9

Summary of the Pharmacokinetic Parameters of Plasma Oxymorphone for Treatments A and C

| Pharmacokinetic Parameters | Plasma Oxymorphone | | | | | |
|---|---|---|---|---|---|---|
| | Treatment D | | Treatment C | | | |
| | Arithmetic Mean | SD | Arithmetic Mean | SD | 90% CI | Mean Ratio |
| Cmax(ng/ml) | 3.2733 | 1.3169 | 2.2635 | 1.0008 | 129.7-162.3 | 146.0 |
| Tmax(hr) | 1.11 | 0.768 | 0.978 | 1.14 | | |
| Auc(0-24)(ng * hr/ml) | 17.30 | 5.259 | 12.39 | 4.116 | 128.5-150.3 | 139.4 |

TABLE 9-continued

Summary of the Pharmacokinetic Parameters of Plasma
Oxymorphone for Treatments A and C

|  | Plasma Oxymorphone | | | | | |
|---|---|---|---|---|---|---|
|  | Treatment D | | Treatment C | | | |
| Pharmacokinetic Parameters | Arithmetic Mean | SD | Arithmetic Mean | SD | 90% CI | Mean Ratio |
| AUC(0-t)(ng * hr/ml) | 19.20 | 6.030 | 14.53 | 4.909 | 117.9-146.5 | 132.2 |
| AUC(0-inf) (ng * hr/ml) | 25.86 | 10.03 | 18.70 | 6.618 | 118.6-146.6 | 132.6 |
| T 1/2el(hr) | 20.6 | 19.3 | 16.2 | 11.4 | 87.3-155.9 | 121.6 |

Treatment D = 10 mg/6.7 ml oxymorphone HCl Oral Solution, Fed: Dose Normalized to 20 mg: test.
Treatment C = 10 mg/6.7 ml oxymorphone HCl Oral Solution, Fasted: Dose Normalized to 20 mg: reference.

The relative bioavailability calculations are summarized in Table 10.

TABLE 10

Mean (S.D.) Relative Oxymorphone Bioavailability
Determined from AUC (0-inf) and AUC (0-24)

|  | Frel BA | | Frel AC | | Frel BD | | Frel DC | |
|---|---|---|---|---|---|---|---|---|
| AUC(0-inf) | 1.169 | (0.2041) | 1.040 | (0.1874) | 0.8863 | (0.2569) | 1.368 | (0.4328) |
| AUC(0-24) | 1.299 | (0.4638) | (0.9598) | (0.2151) | 0.8344 | (0.100) | 1.470 | (0.3922) |

The objectives of this study were to assess the relative bioavailability of oxymorphone from oxymorphone sustained release (20 mg) compared to oxymorphone oral solution (10 mg) under both fasted and fed conditions, and to determine the effect of food on the bioavailability of oxymorphone from the sustained release formulation and from the oral solution.

The presence of a high fat meal had a substantial effect on the oxymorphone Cmax, but less of an effect on oxymorphone AUC from oxymorphone sustained release tablets. Least Squares (LS) mean Cmax was 58% higher and LS mean AUC(0-t) and AUC(0-inf) were 18% higher for the fed condition (Treatment B) compared to the fasted condition (Treatment A) based on LN-transformed data. This was consistent with the relative bioavailability determination from AUC (0-inf) since mean Frel was 1.17. Individual Frel values based on AUC (0-24) were similar (less than 20% different) to Frel values based on AUC (0-inf) for all but 2 subjects. Comparison of mean Frel from AUC (0-inf) to mean Frel from AUC (0-24) is misleading, because not all subjects had a value for AUC (0-inf). Mean Tmax values were similar (approximately 5.6 hours), and no significant different in Tmax was shown using nonparametric analysis. Half value durations were significantly different between the two treatments.

The effect of food on oxymorphone bioavailability from the oral solution was more pronounced, particularly in terms of AUC. LS mean Cmax was 50% higher and LS mean AUC(0-t) and AUC(0-inf) were 32-34% higher for the fed condition (Treatment D) compared to the fasted condition (Treatment C) based on LN-transformed data. This was consistent with the relative bioavailability determination from AUC(0-inf) since mean Frel was 1.37. Individual Frel values based on AUC(0-24) were similar (less than 20% different) to Frel values based on AUC(0-inf.) for all but 5 subjects. Comparison of mean Frel from AUC(0-inf) to mean Frel from AUC(0-24) is misleading because not all subjects had a value for AUC(0-inf). Mean Tmax (approximately 1 hour) was similar for the two treatments and no significant difference was shown.

Under fasted conditions, oxymorphone sustained release 20 mg tablets exhibited similar extent of oxymorphone availability compared to 10 mg oxymorphone oral solution normalized to a 20 mg dose (Treatment A versus Treatment C). From LN-transformed data, LS mean AUC(0-t) was 17% higher for oxymorphone sustained release, whereas LS mean AUC(0-inf) values were nearly equal (mean ratio=99%). However, AUC(0-t) is not the best parameter to evaluate bioavailability since the plasma concentrations were measured for 48 hours for the sustained release formulation versus 36 hours for the oral solution. Mean Frel values calculated from AUC(0-inf) and AUC(0-24), (1.0 and 0.96, respectively) also showed similar extent of oxymorphone availability between the two treatments.

There were differences in parameters reflecting rate of absorption. LS mean Cmax was 49% lower for oxymorphone sustained release tablets compared to the dose-normalized oral solution, based on LN-transformed data. Half-value duration was significantly longer for the sustained release formulation (means, 12 hours versus 2.5 hours).

Under fed conditions, oxymorphone availability from oxymorphone sustained release 20 mg was similar compared to 10 mg oxymorphone oral solution normalized to a 20 mg dose (Treatment B versus Treatment D). From LN-transformed data, LS mean AUC(0-inf) was 12% lower for oxymorphone sustained release. Mean Frel values calculated from AUC(0-inf) and AUC(0-24), (0.89 and 0.83 respectively) also showed similar extent of oxymorphone availability from the tablet. There were differences in parameters reflecting rate of absorption. LS mean Cmax was 46% lower for oxymorphone sustained release tablets compared to the dose-normalized oral solution, based on LN-transformed data. Mean Tmax was 5.7 hours for the tablet compared to 1.1 hours for the oral solution. Half-value duration was significantly longer for the sustained release formulation (means, 7.8 hours versus 3.1 hours).

The presence of a high fat meal did not appear to substantially affect the availability following administration of oxymorphone sustained release tablets. LS mean ratios were 97% for AUC(0-t) and 91% for Cmax (Treatment B versus A), based on LN-transformed data. This was consistent with the relative bioavailability determination from AUC(0-24), since mean Frel was 0.97. AUC(0-inf) was not a reliable measure for bioavailability since half-life could not be estimated accurately, and in many cases at all. Half-life estimates were not accurate because in the majority of subjects, the values for half-life were nearly as long or longer (up to 2.8 times longer) as the sampling period. Mean Tmax was later for the fed treatment compared to the fasted treatment (5.2 and 3.6 hours, respectively), and difference was significant.

Under fasted conditions, oxymorphone sustained release 20 mg tablets exhibited similar availability compared to 10 mg oxymorphone oral solution normalized to a 20 mg dose (Treatment A versus Treatment C). From LN-transformed data, LS mean ratio for AUC (0-t) was 104.5%. Mean Frel (0.83) calculated from AUC(0-24) also showed similar extent of oxymorphone availability between the two treatments. There were differences in parameters reflecting rate of absorption. LS mean Cmax was 57% lower for oxymorphone sustained release tablets compared to the dose-normalized oral solution. Mean Tmax was 3.6 hours for the tablet compared to 0.88 for the oral solution. Half-value duration was significantly longer for the sustained release formulation (means, 11 hours versus 2.2 hours).

Under fed conditions, availability from oxymorphone sustained release 20 mg was similar compared to 10 mg oxymorphone oral solution normalized to a 20 mg dose (Treatment B versus Treatment D). From LN-transformed data, LS mean AUC(0-t) was 14% higher for oxymorphone sustained release. Mean Frel (0.87) calculated from AUC (0-24) also indicated similar extent of availability between the treatments. There were differences in parameters reflecting rate of absorption. LS mean Cmax was 40% lower for oxymorphone sustained release tablets compared to the dose-normalized oral solution. Mean Tmax was 5.2 hours for the tablet compared to 1.3 hour for the oral solution. Half-value duration was significantly longer for the sustained release formulation (means, 14 hours versus 3.9 hours).

The extent of oxymorphone availability from oxymorphone sustained release 20 mg tablets was similar under fed and fasted conditions since there was less than a 20% difference in LS mean AUC(0-t) and AUC(0-inf) values for each treatment, based on LN-transformed data. Tmax was unaffected by food; however, LS mean Cmax was increased 58% in the presence of the high fat meal. Both rate and extent of oxymorphone absorption from the oxymorphone oral solution were affected by food since LS mean Cmax and AUC values were increased approximately 50 and 30%, respectively. Tmax was unaffected by food. Under both fed and fasted conditions, oxymorphone sustained release tablets exhibited similar extent of oxymorphone availability compared to oxymorphone oral solution since there was less than a 20% difference in LS mean AUC(0-t) and AUC(0-inf) values for each treatment.

Bioavailability following oxymorphone sustained release 20 mg tablets was also similar under fed and fasted conditions since there was less than a 20% difference in LS mean Cmax and AUC values for each treatment. Tmax was later for the fed condition. The presence of food did not affect the extent of availability from oxymorphone oral solution since LS mean AUC values were less than 20% different. However, Cmax was decreased 35% in the presence of food. Tmax was unaffected by food. Under both fed and fasted conditions, oxymorphone sustained release tablets exhibited similar extent of availability compared to oxymorphone oral solution since there was less than a 20% difference in LS mean AUC values for each treatment.

Various modifications of the invention, in addition to those described herein, will be apparent to one skilled in the art from the foregoing description. Such modifications are intended to fall within the scope of the appended claims.

What is claimed is:

1. An oral sustained release formulation comprising from about 5 mg to about 80 mg oxymorphone hydrochloride and from about 80 mg to about 360 mg of a granulated sustained release delivery system, wherein the granulated sustained release delivery system comprises from about 8.3% to about 41.7% by weight locust bean gum, from about 8.3% to about 41.7% by weight xanthan gum, from about 20% to about 55% by weight dextrose, from about 5% to about 20% by weight calcium sulfate dihydrate, and from about 2% to about 10% ethyl cellulose.

2. The oral sustained release formulation of claim 1, comprising about 20 mg oxymorphone hydrochloride.

3. The oral sustained release formulation of claim 1, comprising about 160 mg of the granulated sustained release delivery system.

4. An oral sustained release formulation comprising from about 5 to about 80 mg oxymorphone hydrochloride and from about 80 mg to about 360 mg of a granulate sustained release delivery system, wherein the granulated sustained release delivery system comprises about 25% locust bean gum, about 25% xanthan gum, about 35% dextrose, about 10% calcium sulfate dihydrate, and about 5% ethyl cellulose.

5. The oral sustained release formulation of claim 1, further comprising an outer coating.

6. A method for treating a patient suffering from pain comprising administering an effective amount of the oral sustained release formulation of any one of claims 1-5.

7. An oral sustained release formulation comprising from about 5 mg to about 80 mg oxymorphone hydrochloride and from about 300 mg to about 420 mg of a granulated sustained release delivery system, wherein the granulated sustained release delivery system comprises from about 8.3% to about 41.7% by weight locust bean gum, from about 8.3% to about 41.7% by weight xanthan gum, from about 20% to about 55% by weight dextrose, from about 5% to about 20% by weight calcium sulfate dihydrate, and from about 2% to about 10% ethyl cellulose.

8. The oral sustained release formulation of claim 7, comprising about 20 mg oxymorphone hydrochloride.

9. The oral sustained release formulation of claim 7, comprising about 360 mg of the granulated sustained release delivery system.

10. The oral sustained release formulation of claim 7, wherein the granulated sustained release delivery system comprises about 25% locust bean gum, about 25% xanthan gum, about 35% dextrose, about 10% calcium sulfate dihydrate, and about 5% ethyl cellulose.

11. The oral sustained release formulation of claim 7, further comprising an outer coating.

12. A method for treating a patient suffering from pain comprising administering an effective amount of the oral sustained release formulation of any one of claims 7-11.

13. A solid dosage formulation comprising the oral sustained release formulation of any one of claims 1-5.

14. The solid dosage formulation of claim 13, wherein the solid dosage formulation is a tablet.

15. A solid dosage formulation comprising the oral sustained release formulation of anyone of claims 7-11.

16. The solid dosage formulation of claim 15, wherein the solid dosage formulation is a tablet.

* * * * *

UNITED STATES PATENT AND TRADEMARK OFFICE
CERTIFICATE OF CORRECTION

| | | |
|---|---|---|
| PATENT NO. | : 7,276,250 B2 | |
| APPLICATION NO. | : 10/189932 | |
| DATED | : October 2, 2007 | |
| INVENTOR(S) | : Anand R. Baichwal et al. | |

It is certified that error appears in the above-identified patent and that said Letters Patent is hereby corrected as shown below:

Delete title page containing an illustrative figure and substitute the attached title page therefor.

Delete figure 1 and substitute the attached figure 1 therefor.

Please replace Claim 15 at Column 22, line 3 with the following claim:

15. A solid dosage formulation comprising the oral sustained release formulation of any one of claims 7-11.

Signed and Sealed this

Eighth Day of June, 2010

David J. Kappos
*Director of the United States Patent and Trademark Office*

Please replace Table 6 at Column 14, with the below table:

TABLE 6

| Summary of the Pharmacokinetic Parameters of Plasma Oxymorphone for Treatments B and A | | | | | | |
|---|---|---|---|---|---|---|
| | ----- Plasma Oxymorphone ----- | | | | | |
| | Treatment B | | Treatment A | | | |
| Pharmacokinetic Parameters | Arithmetic Mean | SD | Arithmetic Mean | SD | 90% CI | Mean Ratio |
| Cmax(ng/ml) | 1.7895 | 0.6531 | 1.1410 | 0.4537 | 125.4-191.0 | 158.2 |
| Tmax(hr) | 5.65 | 9.39 | 5.57 | 7.14 | | |
| Auc(0-24)(ng*hr/ml) | 14.27 | 4.976 | 11.64 | 3.869 | 110.7-134.0 | 122.3 |
| AUC(0-t)(ng*hr/ml) | 19.89 | 6.408 | 17.71 | 8.471 | 100.2-123.6 | 111.9 |
| AUC(0-inf)(ng*hr/ml) | 21.29 | 6.559 | 19.29 | 5.028 | 105.3-133.9 | 119.6 |
| T 1/2el(hr) | 12.0 | 3.64 | 12.3 | 3.99 | 57.4-155.2 | 106.3 |

Treatment B = 1x20 mg oxymorphone sustained release Tablet, Fed: test

Treatment A = 1x20 mg oxymorphone sustained release tablet, Fasted: reference

Please replace the paragraph at Column 15, line 25, with the following paragraph:

The arithmetic means of the plasma oxymorphone pharmacokinetic parameters and the statistical comparisons for Treatment B versus Treatment D are summarized in Table 8.

Please replace Table 8 at Column 15, with the below table:

Table 8

| Summary of the Pharmacokinetic Parameters of Plasma Oxymorphone for Treatments B and D | | | | | | |
|---|---|---|---|---|---|---|
| | ----- Plasma Oxymorphone ----- | | | | | |
| | Treatment B | | Treatment D | | | |
| Pharmacokinetic Parameters | Arithmetic Mean | SD | Arithmetic Mean | SD | 90% CI | Mean Ratio |
| Cmax(ng/ml) | 1.7895 | 0.6531 | 3.2733 | 1.3169 | 42.7-65.0 | 50.0 |
| Tmax(hr) | 5.65 | 9.39 | 1.11 | 0.768 | | |
| Auc(0-24)(ng*hr/ml) | 14.27 | 4.976 | 17.30 | 5.259 | 74.4-90.1 | 82.2 |
| AUC(0-t)(ng*hr/ml) | 19.89 | 6.408 | 19.28 | 6.030 | 92.5-114.1 | 103.3 |
| AUC (0-inf) (ng*hr/ml) | 21.29 | 6.559 | 25.86 | 10.03 | 75.0-95.2 | 85.1 |
| T 1/2el(hr) | 12.0 | 3.64 | 20.6 | 19.3 | 31.9-86.1 | 59.0 |

Treatment B = 1x20 mg oxymorphone sustained release Tablet, Fed: test
Treatment D = 1x20 mg/6.7ml oxymorphone HCl Oral Solution, Fed: Dose Normalized to 20 mg: reference.

Please delete Table 9 at Column 15, and replace it with the following table:

Table 9

| Summary of the Pharmacokinetic Parameters of Plasma Oxymorphone for Treatments D and C | | | | | | |
|---|---|---|---|---|---|---|
| | --- Plasma Oxymorphone --- | | | | | |
| | Treatment D | | Treatment C | | | |
| Pharmacokinetic Parameters | Arithmetic Mean | SD | Arithmetic Mean | SD | 90% CI | Mean Ratio |
| Cmax(ng/ml) | 3.2733 | 1.3169 | 2.2635 | 1.0008 | 129.7-162.3 | 146.0 |
| Tmax(hr) | 1.11 | 0.768 | 0.978 | 1.14 | | |
| Auc(0-24)(ng*hr/ml) | 17.30 | 5.259 | 12.39 | 4.116 | 128.5-150.3 | 139.4 |
| AUC(0-t)(ng*hr/ml) | 19.20 | 6.030 | 14.53 | 4.909 | 117.9-146.5 | 132.2 |
| AUC (0-inf) (ng*hr/ml) | 25.86 | 10.03 | 18.70 | 6.618 | 118.6-146.6 | 132.6 |
| T 1/2el(hr) | 20.6 | 19.3 | 16.2 | 11.4 | 87.3-155.9 | 121.6 |

Treatment D = 10 mg/6.7 ml oxymorphone HCl Oral Solution, Fed: Dose Normalized to 20 mg: test.

Treatment C = 10 mg/6.7 ml oxymorphone HCl Oral Solution, Fed: Dose Normalized to 20 mg: reference.

(12) United States Patent
Baichwal et al.

(10) Patent No.: US 7,276,250 B2
(45) Date of Patent: Oct. 2, 2007

(54) SUSTAINED RELEASE FORMULATIONS OF OXYMORPHONE

(75) Inventors: Anand R. Baichwal, Wappingers Falls, NY (US); Hual-Hung Kao, Syosset, NY (US); Troy W. McCall, Germantown, TN (US)

(73) Assignee: Penwest Pharmaceuticals Company, Danbury, CT (US)

(*) Notice: Subject to any disclaimer, the term of this patent is extended or adjusted under 35 U.S.C. 154(b) by 216 days.

(21) Appl. No.: 10/189,932

(22) Filed: Jul. 3, 2002

(65) Prior Publication Data
US 2003/0129230 A1    Jul. 10, 2003

Related U.S. Application Data

(60) Provisional application No. 60/329,352, filed on Oct. 15, 2001, provisional application No. 60/329,426, filed on Oct. 15, 2001, provisional application No. 60/303,357, filed on Jul. 6, 2001.

(51) Int. Cl.
*A61K 9/22* (2006.01)
*A61K 9/26* (2006.01)
*A61K 9/36* (2006.01)

(52) U.S. Cl. ............ 424/468; 424/470; 424/464; 424/479; 424/480; 424/481; 424/482

(58) Field of Classification Search ............ 424/468, 424/474, 490, 475, 476, 477, 479, 480, 482, 424/491, 494, 495, 497, 498
See application file for complete search history.

(56) References Cited

U.S. PATENT DOCUMENTS

| | | | |
|---|---|---|---|
| 2,806,033 A | 9/1957 | Lewenstein et al. | |
| 3,393,197 A | 7/1968 | Pachter et al. | |
| 3,845,770 A | 11/1974 | Theeuwes et al. | |
| 3,879,555 A | 4/1975 | Pachter et al. | |
| 3,966,940 A | 6/1976 | Pachter et al. | |
| 3,980,766 A | 9/1976 | Shaw et al. | |
| 4,070,494 A | 1/1978 | Hoffmeister et al. | |
| 4,366,159 A | 12/1982 | Magruder | |
| 4,457,933 A | 7/1984 | Gordon et al. | |
| 4,464,376 A | 8/1984 | Sunshine et al. | |

(Continued)

FOREIGN PATENT DOCUMENTS

AU    0016639    12/1999

(Continued)

OTHER PUBLICATIONS

Staniforth, et al., "Synergistically Interacting Heterodisperse Polysaccharides—Function in Achieving Controllable Drug Delivery," *American Chemical Society*, pp. 327-350 (1993).

(Continued)

*Primary Examiner*—Lakshmi S. Channavajjala
(74) *Attorney, Agent, or Firm*—Wilmer Cutler Pickering Hale & Dorr, LLP

(57) ABSTRACT

Sustained release formulations of oxymorphone or pharmaceutically acceptable salts thereof; methods for making the sustained release formulations of oxymorphone or pharmaceutically acceptable salts thereof; and methods for using the sustained release formulations of oxymorphone or pharmaceutically acceptable salts thereof to treat patients suffering from pain are provided.

16 Claims, 1 Drawing Sheet

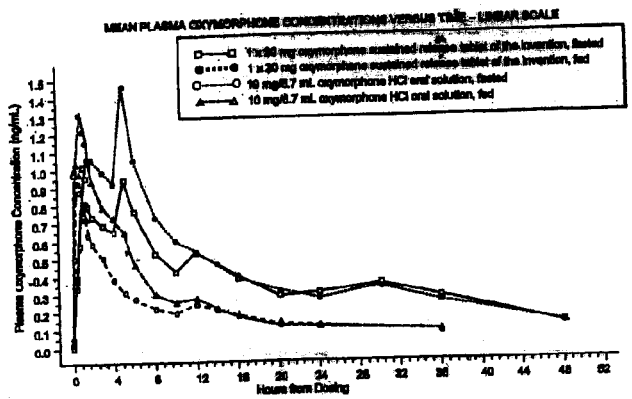

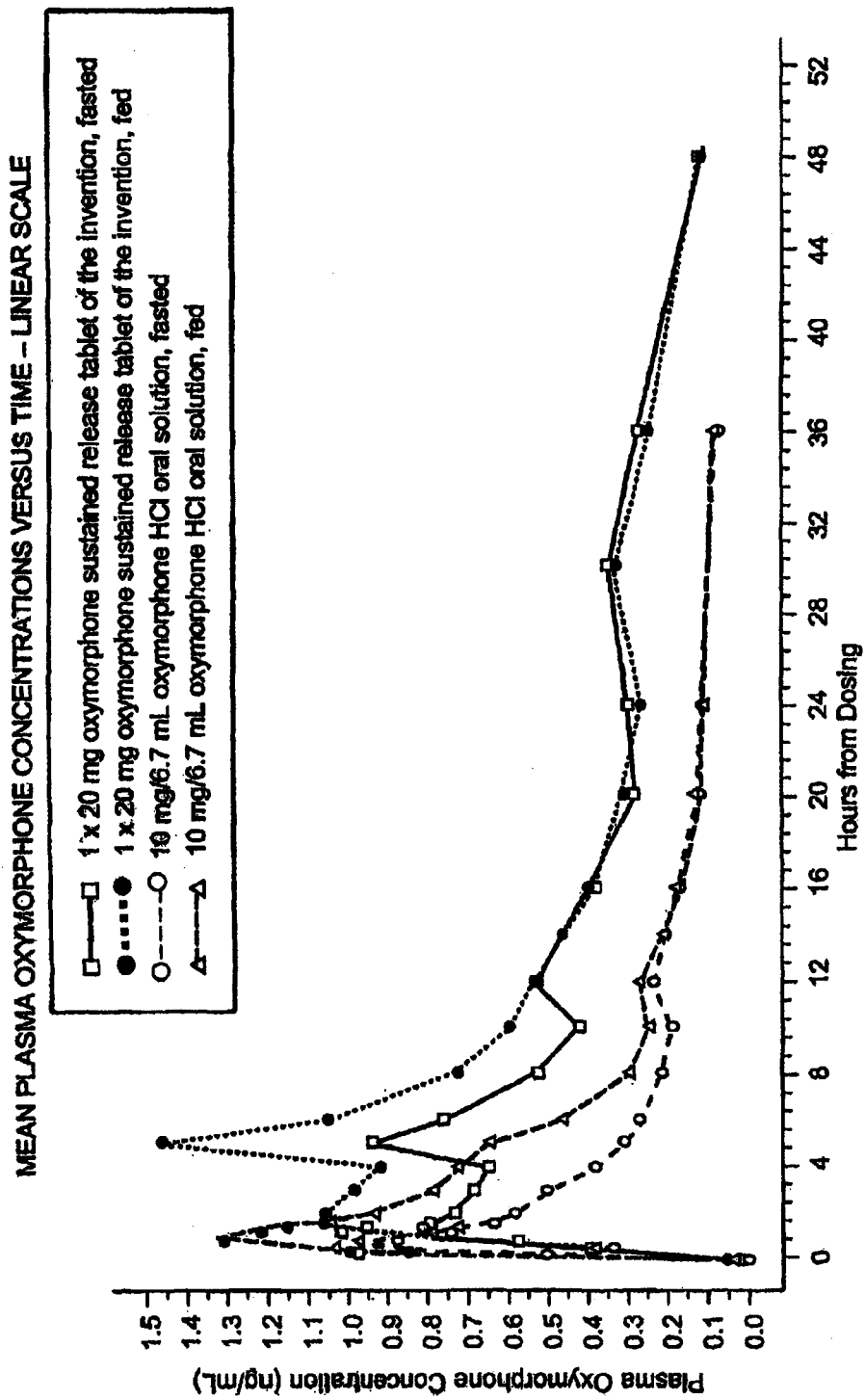
CORRECTED FIGURE 1